US 9,004,684 B2

(12) United States Patent
Iwanaga et al.

(10) Patent No.: US 9,004,684 B2
(45) Date of Patent: Apr. 14, 2015

(54) FUNDUS CAMERA

(75) Inventors: Tomoyuki Iwanaga, Yokohama (JP);
Nobuyoshi Kishida, Musasahino (JP);
Hideyuki Ohban, Kawaguchi (JP);
Shinya Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 384 days.

(21) Appl. No.: 12/428,384

(22) Filed: Apr. 22, 2009

(65) Prior Publication Data
US 2009/0268160 A1 Oct. 29, 2009

(30) Foreign Application Priority Data

Apr. 24, 2008 (JP) .................. 2008-113940

(51) Int. Cl.
*A61B 3/10* (2006.01)
*A61B 3/14* (2006.01)
*A61B 3/00* (2006.01)
*A61B 3/12* (2006.01)

(52) U.S. Cl.
CPC ............... *A61B 3/14* (2013.01); *A61B 3/0075* (2013.01); *A61B 3/12* (2013.01)

(58) Field of Classification Search
USPC .................. 351/206, 211, 220, 221, 205, 208
See application file for complete search history.

(56) References Cited

U.S. PATENT DOCUMENTS

| | | | | | |
|---|---|---|---|---|---|
| 5,594,512 | A | * | 1/1997 | Yoneda et al. | 351/206 |
| 5,694,198 | A | * | 12/1997 | Ueno | 351/221 |
| 5,706,071 | A | * | 1/1998 | Tokunaga | 351/206 |
| 7,347,553 | B2 | * | 3/2008 | Matsumoto | 351/214 |
| 2006/0170865 | A1 | * | 8/2006 | Hirohara et al. | 351/205 |
| 2007/0291226 | A1 | * | 12/2007 | Fujii et al. | 351/210 |

FOREIGN PATENT DOCUMENTS

| | | |
|---|---|---|
| JP | 03-060632 A | 3/1991 |
| JP | 5-095907 A | 4/1993 |
| JP | 2001-008900 A | 1/2001 |

* cited by examiner

*Primary Examiner* — Mahidere Sahle
(74) *Attorney, Agent, or Firm* — Canon U.S.A., Inc. IP Division

(57) ABSTRACT

A fundus camera includes a focus target projection unit including a focus target located at a position conjugate with a fundus of a subject's eye, a split optical element configured to split a light flux passing through the focus target, and a focus target illumination light source configured to illuminate the focus target, a fundus photographing optical system including a focusing lens, a focus link mechanism configured to interlockingly move the focus target projection unit and the focusing lens in a direction of an optical axis, at least two lenses located behind a plane optically conjugate with the imaging plane of the fundus photographing optical system and outside an optical axis of the fundus photographing optical system, image sensors respectively located behind the two lenses, and a phase difference detection unit configured to detect a phase difference between the focus target images based on signals output from the image sensors.

51 Claims, 8 Drawing Sheets

FUNDUS CAMERA

BACKGROUND OF THE INVENTION

1. Field of the Invention

The present invention relates to a fundus camera used for photographing a fundus of a subject's eye in an ophthalmologist's office or the like.

2. Description of the Related Art

Hitherto, techniques for facilitating focusing a fundus camera on a subject's eye have been known. For example, first, a focus split target is projected onto the pupil of a subject's eye, on which split images of the focus split target are formed. Then, the split target images are observed via a focusing lens of an observing/photographing system. Thus, focusing is performed by observing a positional relationship of the focus split target images.

Japanese Patent Application Laid-Open No. 5-95907 discusses a known fundus camera that captures projected focus split images and that performs autofocusing based on the positional relationship of the focus split images. More particularly, the fundus camera captures two split images of a focus split target projected onto a fundus and detects a focus state based on positions of the two focus split target images. At that time, brightness of the target is attenuated.

Further, Japanese Patent Application Laid-Open No. 8-275921 discusses an ophthalmologic apparatus that projects a focus target onto a fundus of a subject's eye and captures a target image using a photographic optical system to detect a focus state.

Hitherto, a fundus camera has been known, which has a unit for projecting a light flux of a focus split target onto a fundus of a subject's eye, on which split images of the focus split target are formed, and a unit having a focusing lens for observing/photographing the fundus. Both of the units can be moved in the direction of an optical axis interlockingly with each other. Then, focus split target images formed on the fundus of the subject's eye are observed and brought into a predetermined positional relationship, for example, aligned with each other. Thus, the fundus camera can easily be focused on the fundus of the subject's eye. In addition, an apparatus has been known, which captures focus split images and performs autofocusing by detecting the position of each focus split image.

However, to eliminate reflection light from the cornea of a subject's eye, conventional fundus cameras are constructed such that a fundus illumination light flux or a focus slit target light flux and an observing/photographing light flux are respectively incident upon different areas in the vicinity of the pupil of a subject's eye. Accordingly, in a case where an aberration of an optical system of a subject's eye varies among individuals, when the fundus of a subject's eye is photographed only with the positions of the focus split target images set in a predetermined positional relationship, a focusing error may be caused depending on subject's eyes. Consequently, a fundus image may be out of focus.

SUMMARY OF THE INVENTION

The present invention is directed to a fundus camera capable of achieving accurate focusing even in a case where a subject's eye has an aberration.

According to an aspect of the present invention, a fundus camera includes a focus target projection unit including a focus target located at a position conjugate with a fundus of a subject's eye, a split optical element configured to split a light flux passing through the focus target, and a focus target illumination light source configured to illuminate the focus target, a fundus photographing optical system including at least an objective lens, a focusing lens, and a photographic lens, a focus link mechanism configured to interlockingly move the focus target projection unit and the focusing lens in a direction of an optical axis such that the fundus, the focus target, and an imaging plane of the fundus photographing optical system are optically conjugate with one another, at least two lenses located behind a plane optically conjugate with the imaging plane of the fundus photographing optical system and outside an optical axis of the fundus photographing optical system to capture focus target images on the fundus from the focus target, image sensors respectively located behind the two lenses, and a phase difference detection unit configured to detect a phase difference between the focus target images based on a difference between signals output from the image sensors.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EMBODIMENTS

Various exemplary embodiments, features, and aspects of the invention will be described in detail below with reference to the drawings.

Figure 1:
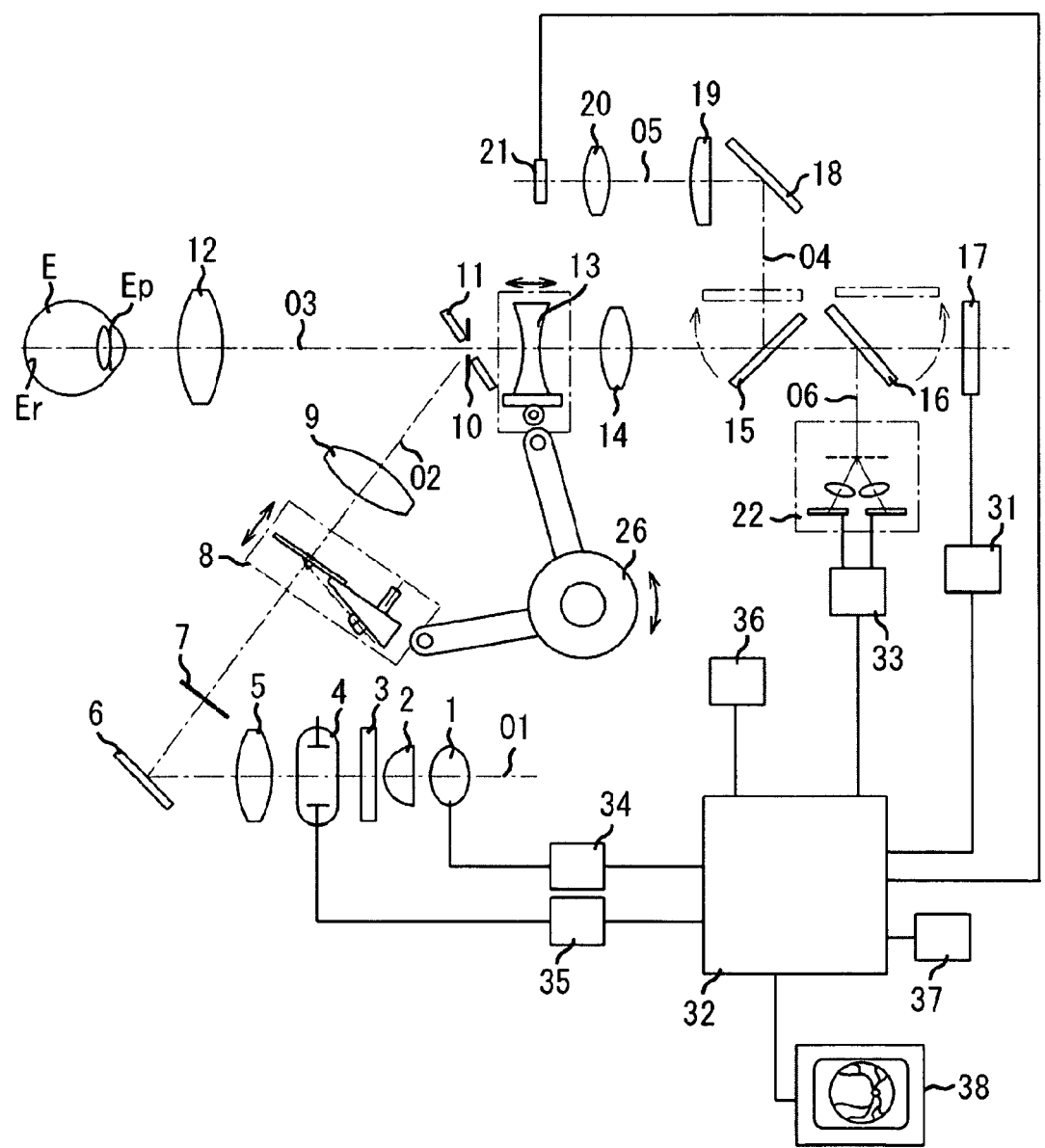
FIG. 1 illustrates a configuration of a fundus camera according to an exemplary embodiment of the present invention.

FIG. 1 illustrates a configuration of a fundus camera according to an exemplary embodiment of the present invention. An observing light source 1, such as a halogen lamp, configured to emit stationary light, a condenser lens 2, a filter 3 configured to transmit infrared light and to interrupt visible light, a photographing light source 4, such as a flash unit, a lens 5, and a mirror 6 are arranged on an optical axis O1. A ring diaphragm 7 having an annular opening, a focus target projection unit 8, a relay lens 9, and a perforated mirror 11 having a central opening, in which a photographing diaphragm 10 is provided, are sequentially arranged on an optical axis O2 extending in a reflection direction from the mirror 6.

On the other hand, an objective lens 12, facing a subject's eye E, is located on an optical axis O3 extending in a reflection direction from the perforated mirror 11. A focusing lens 13, a photographic lens 14, flip-up mirrors 15 and 16, and a still-image image sensor 17 are sequentially arranged behind the central opening of the perforated mirror 11. Thus, a fundus photographing optical system is constructed.

A mirror 18 configured to reflect infrared light and to transmit visible light is located on an optical axis O4 extending in a reflection direction from the flip-up mirror 15. A field lens 19, a lens 20, and an observation-image image sensor 21 are sequentially arranged on an optical axis O5 extending in a reflection direction from the mirror 18. Thus, a fundus observing optical system is constructed. The still-image image sensor 17 is located at a position optically conjugate with that of the observation-image image sensor 21. In addition, a phase difference detection unit 22 is located on an optical axis O6 extending in a reflection direction from the flip-up mirror 16.

Figure 2A:
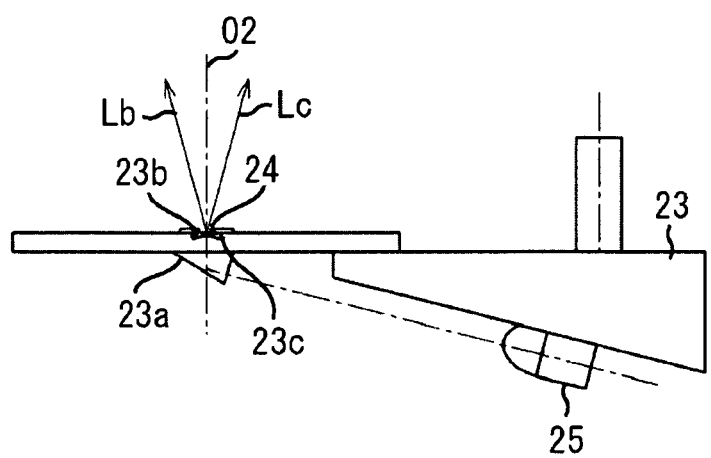
FIGS. 2A and 2B are a side view and a front view of a focus target projection unit, respectively.
Figure 2B:
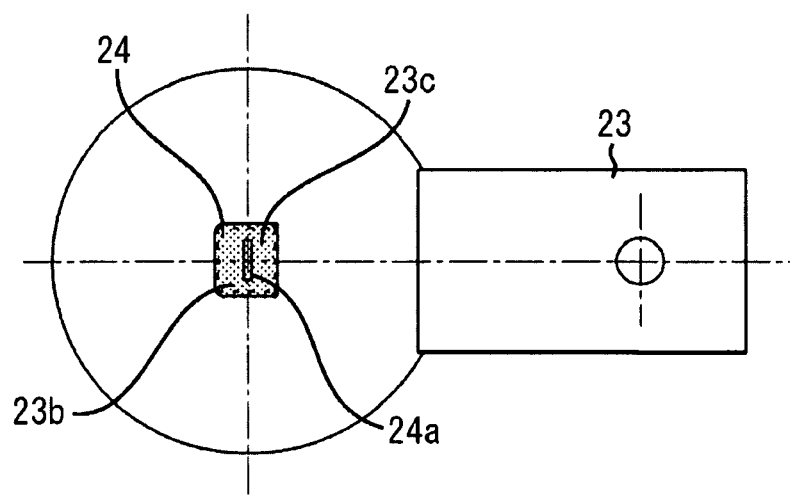

FIG. 2A is a side view of the focus target projection unit 8. FIG. 2B is a front view thereof. As illustrated in FIGS. 2A and 2B, the focus target projection unit 8 includes a focus split prism 23 having prism portions 23a, 23b, and 23c, a focus target 24 having a rectangular opening portion 24a, and a focus target illumination light emitting diode (LED) 25.

The focus target projection unit 8 and the focusing lens 13 are connected to each other by a focus link mechanism 26 and are interlockingly movable in the directions of the optical axes O2 and O3, respectively. The focus link mechanism 26 sets the focus target 24 of the focus target projection unit 8 to be optically conjugate with each of the still-image image sensor 17 and the observation-image image sensor 21.

Figure 3:
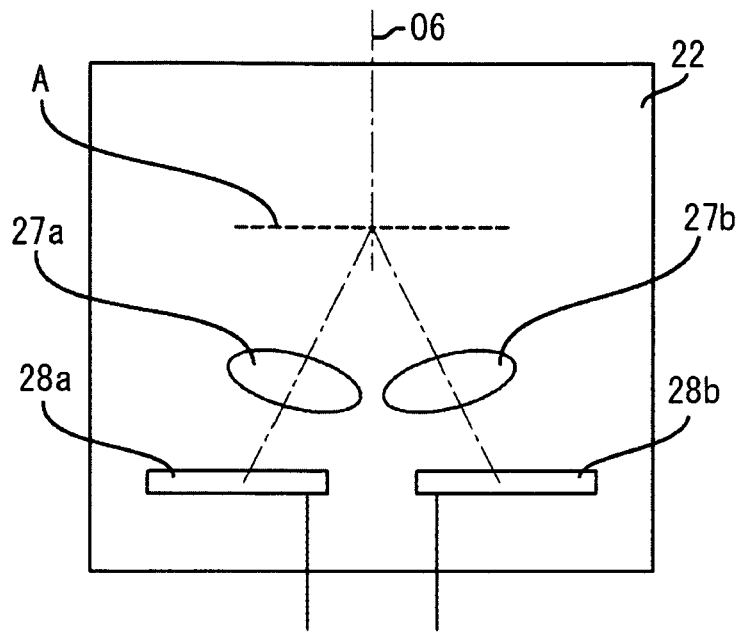
FIG. 3 illustrates a configuration of a phase difference detection unit.

In the phase difference detection unit 22, as illustrated in FIG. 3, a pair of lenses 27a and 27b and one-dimensional sensors 28a and 28b are located outside the optical axis O6 behind a plane A that is optically conjugate with each of the still-image image sensor 17 and the observation-image image sensor 21. The one-dimensional sensors 28a and 28b are provided at positions, which are optically conjugate with the position of the conjugate plane A, via the lenses 27a and 28b, respectively. Thus, a phase difference or deviation between target images respectively formed on the one-dimensional sensors 28a and 28b is detected to obtain a distance therebetween.

An output of the still-image image sensor 17 is connected to a control unit 32 via an image processing unit 31. An output of the observation-image image sensor 21 is connected directly to the control unit 32. An output of each of the one-dimensional sensors 28a and 28b is connected to the control unit 32 via a phase difference computing unit 33.

An output of the control unit 32 is connected to the observing light source 1 via an observing light source control unit 34, which controls adjustment of the amount of light, turn-on, and turn-off thereof. An output of the control unit 32 is also connected to the photographing light source 4 via a photographing light source control unit 35, which controls adjustment of the amount of light, turn-on, and turn-off thereof. An image memory 36, a photographing switch 37, and a monitor 38 are connected to the control unit 32.

Devices other than the monitor 38 and the photographing switch 37 are mounted on an optical base (not shown). Thus, an optical unit of the fundus camera is constructed. The optical unit is mounted on a stage unit.

When a fundus is photographed, the control unit 32 controls the observing light source control unit 34 to turn on the observing light source 1. A light flux emitted from the observing light source 1 is condensed by the condenser lens 2. The filter 3 cuts out visible light of incident light from the photographing light source 4. However, the filter 3 transmits only infrared light thereof. Then, a ring light flux is formed by the lens 5, the mirror 6 and the ring diaphragm 7. The ring light flux passes through the focus target projection unit 8 and the relay lens 9. Then, the light flux is deflected by the perforated mirror 11 in the direction of the optical axis O3. The deflected light flux illuminates the fundus $E_r$ of the subject's eye E via the objective lens 12. The light flux reaching the fundus $E_r$ is reflected and scattered. Then, light to be formed into a fundus reflection image is reflected from the subject's eye E. The fundus reflection image passes through the objective lens 12, the photographing diaphragm 10, the focusing lens 13, and the photographic lens 14. Then, the light is deflected by the flip-up mirror 15 and the mirror 18 in the direction of the optical axis O5. The deflected light is formed into a fundus reflection image on the observation-image image sensor 21 via the field lens 19 and the lens 20. The control unit 32 causes the monitor 38 to display the fundus image captured by the observation-image image sensor 21.

The operator performs fine adjustment of alignment of the optical unit with the subject's eye E while observing the fundus image displayed on the monitor 38. Subsequently, the operator performs focus adjustment, which will be described below. Then, the operator presses the photographing switch 37 to photograph the fundus image.

As illustrated in FIGS. 2A and 2B, a light flux emitted from the focus target illumination LED 25 is deflected in the direction of the optical axis O2 by the prism portion 23a of the focus split prism 23. Then, the deflected light flux reaches each of the prism portions 23b and 23c. The prism portions 23b and 23c function as split optical elements respectively having prism faces the inclination angles of which are symmetrical with respect to the optical axis O2. The light flux reaching each of the prism portions 23b and 23c passes through the rectangular opening portion 24a illustrated in FIGS. 2A and 2B and is split into two focus target light fluxes Lb and Lc that are symmetric with respect to the optical axis O2. Then, the focus target light fluxes Lb and Lc reach the subject's eye E via the relay lens 9, the perforated mirror 11, and the objective lens 12.

Figure 4:
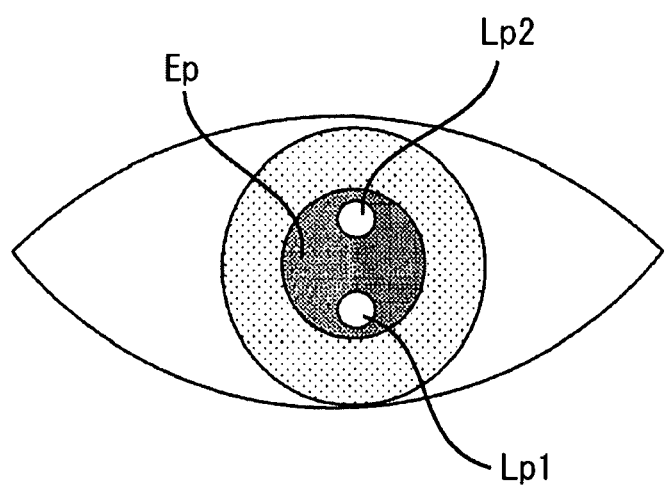
FIG. 4 illustrates a position on a pupil of a subject's eye, through which each focus target light flux passes.

FIG. 4 illustrates a position Lp1 on a pupil $E_p$ of the subject's eye E, through which the focus target light flux Lb passes, and a position Lp2 on the pupil $E_p$ of the subject's eye E, through which the focus target light flux Lc passes.

Figure 5A:
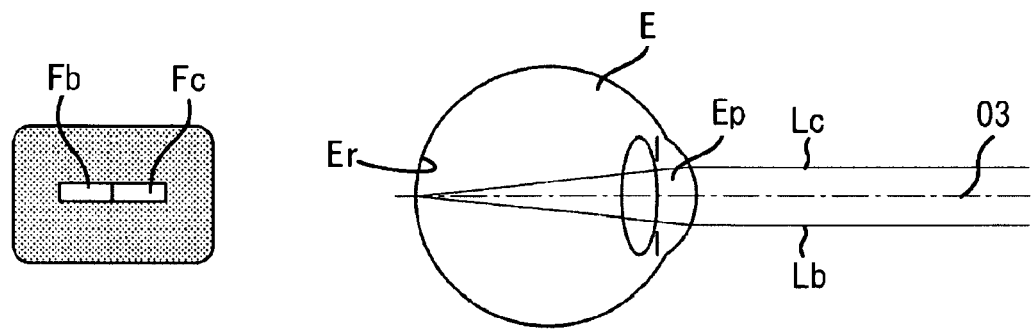
FIGS. 5A through 5C illustrate functions of a focus target.
Figure 5B:
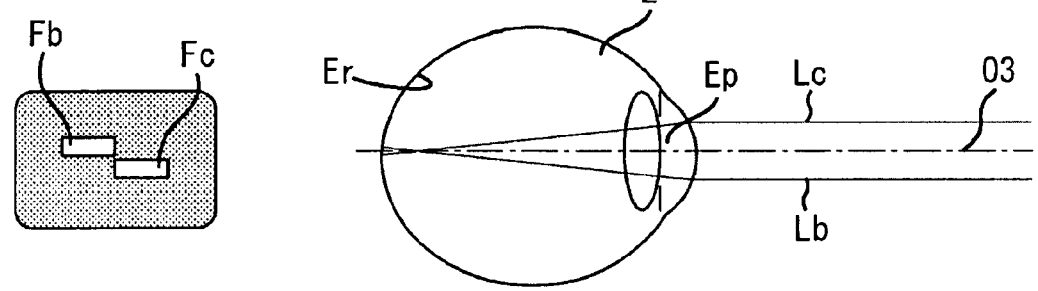
Figure 5C:
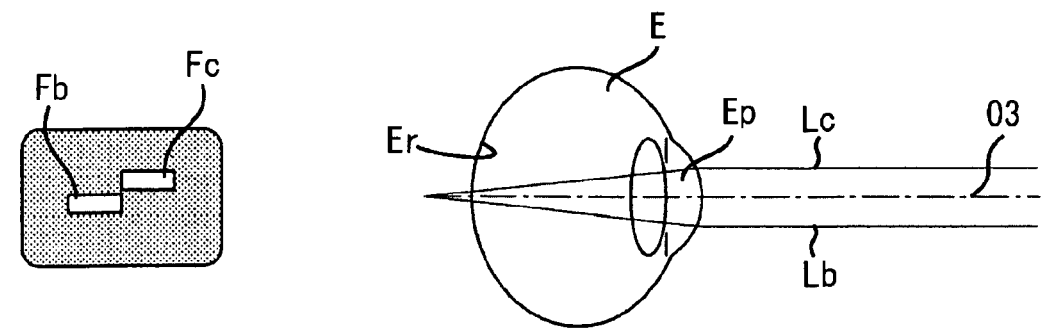

FIGS. 5A through 5C illustrate manners in each of which the focus target fluxes Lb and Lc reach the fundus Er of the subject's eye E, and a relationship between focus target images Fb and Fc on the fundus $E_r$, which are formed from the focus target light fluxes Lb and Lc, respectively.

FIG. 5A illustrates a case where the fundus $E_r$ of the subject's eye E is optically conjugate with the focus target 24. Because the fundus $E_r$ is optically conjugate with the focus target 24, the two split focus target light fluxes Lb and Lc are formed into the target images Fb and Fc of the rectangular opening portion 24a of the focus target 24, which are located in a line, on the fundus $E_r$.

FIG. 5B illustrates a case where the subject's eye E is more near-sighted, as compared with the subject's eye E illustrated in FIG. 5A. Because the fundus $E_r$ in the case illustrated in FIG. 5B is not optically conjugate with the focus target 24, the two split focus target light fluxes Lb and Lc are formed into the target images Fb and Fc on the fundus $E_r$ so that, as viewed in FIG. 5B, the target image Fb is shifted upward from the position thereof illustrated in FIG. 5A, while the target image Fc is shifted downward from the position thereof illustrated in FIG. 5A.

FIG. 5C illustrates a case where the subject's eye E is more far-sighted, as compared with the subject's eye E illustrated in FIG. 5A. Because the fundus $E_r$ in the case illustrated in FIG. 5B is not optically conjugate with the focus target 24, the two split focus target light fluxes Lb and Lc are formed into the target images Fb and Fc on the fundus $E_r$ so that, as viewed in FIG. 5C, the target image Fb is shifted downward from the position thereof illustrated in FIG. 5A, while the target image Fc is shifted upward from the position thereof illustrated in FIG. 5A.

The operator observes the focus target images Fb and Fc displayed on the monitor 38 and manually operates a focusing knob (not shown) such that the focus target images Fb and Fc are located in a line, i.e., that the fundus $E_r$ and the focus target 24 are optically conjugate with each other. The focus target 24 of the focus target projection unit 8, the imaging plane of the still-image image sensor 17, and the fundus $E_r$ are optically conjugate with one another, so that the fundus $E_r$ can be brought into focus.

However, in a case where an optical aberration is large due to spherical aberration, astigmatism, or the like of the subject's eye E, even when the focus target images Fb and Fc are located in a line, the focus target images Fb and Fc may not be brought into best focus on the fundus $E_r$.

Figure 6:
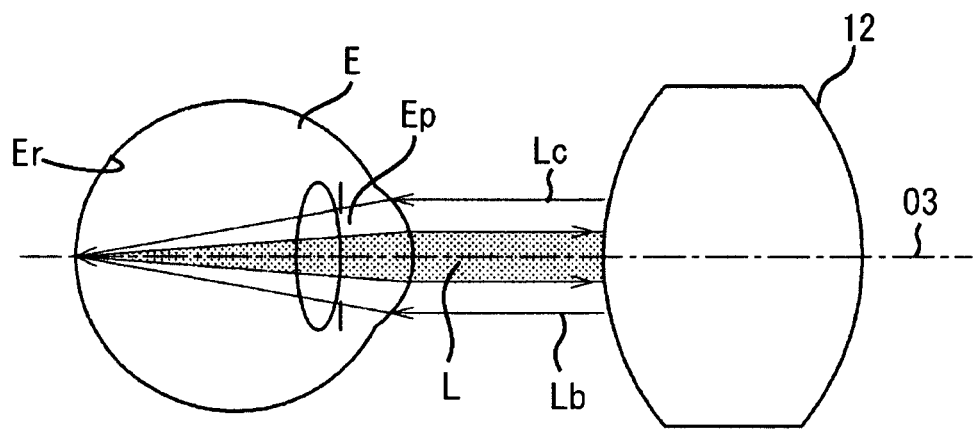
FIG. 6 illustrates a subject's eye, and focus target light fluxes and an observing/photographing light flux in the vicinity of an objective lens.

FIG. 6 illustrates the subject's eye E, and the focus target light fluxes Lb and Lc, and the observing/photographing light flux L in the vicinity of the objective lens 12. The focus target light fluxes Lb and Lc pass through positions on the pupil $E_p$ of the subject's eye E, which are located away from the optical axis O3. The observing/photographing light flux L, which is restricted by the objective lens 12, passes through a position on the pupil $E_p$, which corresponds to the center of the optical axis O3. In a case where the optical aberration of the subject's eye E is small, the depth of focus of the fundus camera is large. The images can be put into focus on the fundus $E_r$ by bringing the focus target images Fb and Fc displayed on the monitor 38 in line.

Figure 7:
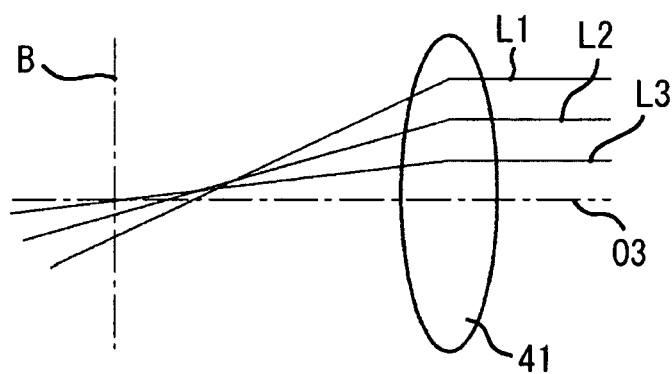
FIG. 7 illustrates a spherical aberration.

FIG. 7 illustrates a spherical aberration. It is assumed that, as viewed in FIG. 7, light rays L1, L2, and L3, which are parallel to the optical axis O and differ from one another in height from the optical axis O, are incident upon the lens 41 from the right side, as viewed in FIG. 7, towards a focal plane B. In a case where the lens 41 has a spherical aberration, the light ray L3, whose height from the optical axis O is lowest, passes through a position on the focal plane B, which is substantially closest to the optical axis O. However, the light rays L1 and L2 pass through positions on the focal plane B, which are located away from the optical axis O.

In a case where the aberration of the subject's eye E is large, the focus target light fluxes Lb and Lc and the observing/photographing light flux L pass through different areas on the pupil $E_p$. Accordingly, even when the focus target images Fb and Fc are located in a line, the images Fb and Fc are affected by the aberration of the lens 41. Thus, the focus target images Fb and Fc are not always brought into best focus on the fundus $E_r$.

Figure 8:
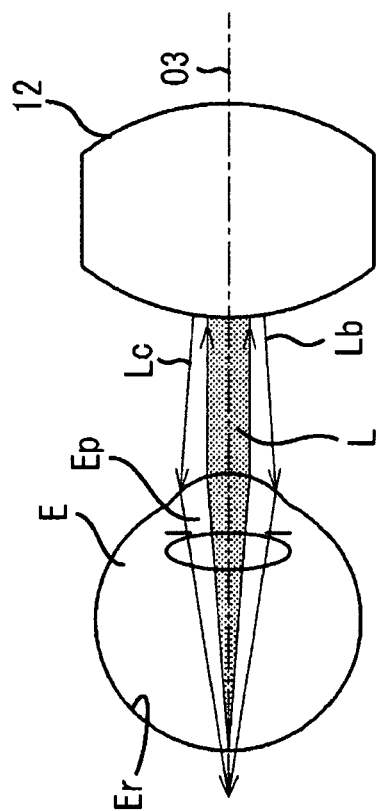
FIG. 8 illustrates a subject's eye having a large spherical aberration, and focus target light fluxes and an observing/photographing light flux in the vicinity of an objective lens.
Figure 8:
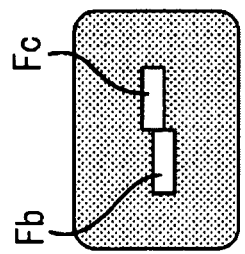

FIG. 8 illustrates the subject's eye E having a large spherical aberration, and the focus target light fluxes Lb and Lc and the observing/photographing light flux L in the vicinity of the objective lens 12. Because the subject's eye E has a large spherical aberration, best focus cannot be achieved by arranging the focus target images Fb and Fc in a line. The images are brought into focus on the fundus $E_r$ by locating the focus target image Fb slightly downward from the position illustrated in FIG. 5A and the focus target image Fc slightly upward from the position illustrated in FIG. 5A.

Thus, aberrations, such as a spherical aberration and astigmatism, of human eyes vary among different individuals. Consequently, in a case where a subject's eye E has a large aberration, focus correction suitable for the aberration of the subject's eye E is required.

Figure 9A:
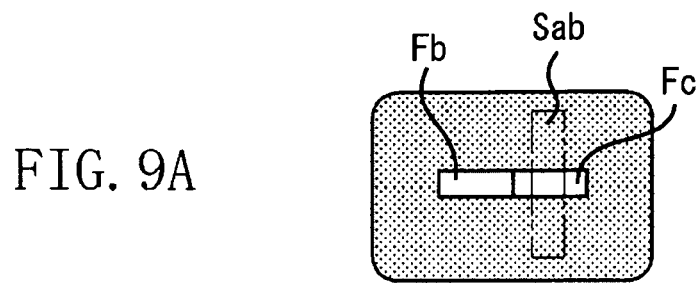
FIGS. 9A through 9C illustrate images of focus targets and one-dimensional sensors, which are projected on a fundus.
Figure 9B:
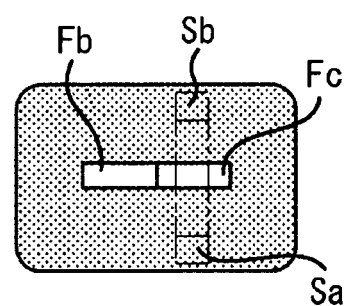
Figure 9C:
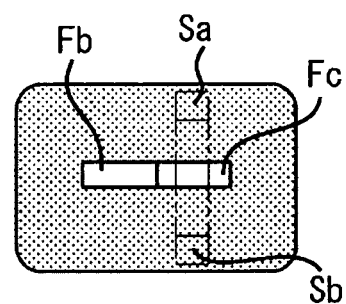

FIGS. 9A through 9C illustrate the focus target images Fb and Fc and images Sab, Sa, and Sb of the one-dimensional sensors 28a and 28b, which are projected on the fundus $E_r$.

Figure 10:
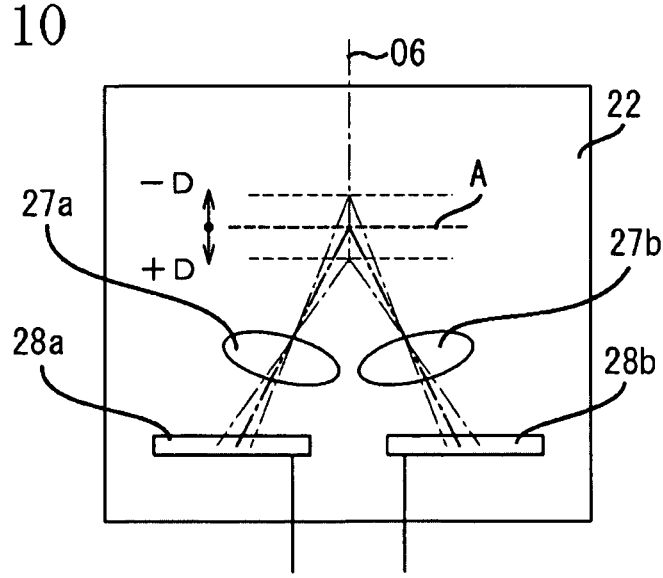
FIG. 10 illustrates a relationship between a phase difference detection unit and a plane conjugate with the fundus.

The operator observes images displayed on the monitor 38. Then, the operator manually operates the focusing knob to locate the focus target images Fb and Fc displayed on the monitor 38 in a line. In a case where the subject's eye E has almost no aberration, the fundus Er, the still-image image sensor 17, and the conjugate plane A of the phase difference detection unit 22 illustrated in FIG. 10 are optically conjugate with one another. As illustrated in FIG. 9A, two images of the one-dimensional sensors 28a and 28b on the fundus Er overlap each other to form the sensor image Sab.

In a case where the subject's eye E has an aberration, the positions of the two sensor images Sa and Sb projected on the fundus Er from the one-dimensional sensors 28a and 28b deviate from each other in an up-down direction, as viewed in FIGS. 9B and 9C. In a case where the conjugate plane of the fundus $E_r$ is located in the front vicinity of the conjugate plane A, as illustrated in FIG. 10, the sensor image Sa is shifted downward, while the sensor image Sb is shifted upward, as viewed in FIG. 9B. On the other hand, in a case where the conjugate surface of the fundus $E_r$ is located in the rear vicinity of the conjugate plane A, the sensor image Sa is shifted upward, while the sensor image Sb is shifted downward, as viewed in FIG. 9C.

Figure 11A:
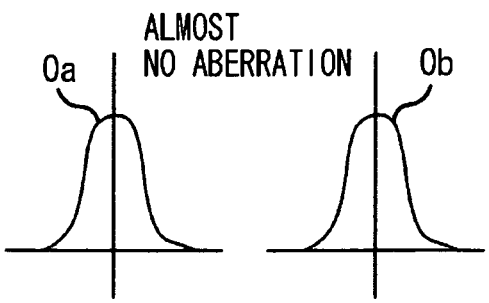
FIGS. 11A through 11C illustrate output signals from the one-dimensional sensor.
Figure 11B:
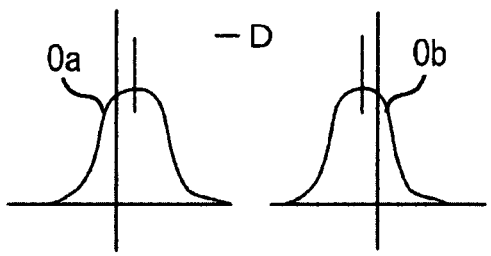
Figure 11C:
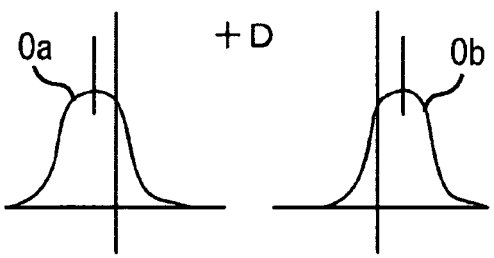

FIGS. 11A through 11C illustrate waveforms of signals to be output to the control unit 32 from the one-dimensional sensors 28a and 28b, respectively corresponding to the cases illustrated in FIGS. 9A through 9C. In a case where the subject's eye E has almost no aberration, when the focus target images Fb and Fc are located in a line, output signals Oa and Ob of the two one-dimensional sensors 28a and 28b have substantially the same waveform, as illustrated in FIG. 11A.

In a case where the subject's eye E has an aberration and where the conjugate plane of the fundus $E_r$ is located in the front vicinity of the conjugate plane A, when the focus target images Fb and Fc are located in a line, output signals Oa and Ob of the two one-dimensional sensors 28a and 28b have different phases, as illustrated in FIG. 11B. That is, the output signal Oa is delayed in phase, while the output signal Ob is advanced in phase. On the other hand, in a case where the subject's eye E has an aberration and where the conjugate plane of the fundus $E_r$ is located in the rear vicinity of the conjugate plane A, when the focus target images Fb and Fc are located in a line, output signals Oa and Ob of the two one-dimensional sensors 28a and 28b have different phases, as illustrated in FIG. 11C. That is, the output signal Oa is advanced in phase, while the output signal Ob is delayed in phase. The output signals Oa and Ob are input to the phase difference computing unit 33, at which a phase difference therebetween is calculated. Consequently, a focus deviation amount can be obtained.

So far, the general procedure performed by the fundus camera, and the functions of the focus target projection unit 8 and the phase difference detection unit 22 have been described. In addition, it has been described that focus correction suitable for individual difference in aberrations of human eyes can be achieved by combining such functions. That is, according to the procedure, first, the fine adjustment of alignment of the optical unit with a subject's eye E is performed. Subsequently, an operator operates a focusing knob such that focus target images Fb and Fc displayed on the monitor 38 are located in a line. Thus, first focus adjustment is performed. However, in a case where the subject's eye E has an aberration, as described above, best focus may not be achieved by such adjustment of focus of an image on the fundus $E_r$. However, according to the present embodiment, focus correction suitable for individual difference in aberrations of human eyes can be implemented.

When the operator presses the photographing switch 37 upon completion of the first focus adjustment, the control unit 32 causes the flip-up mirror 15 to flip up to a position indicated by dashed-dotted line in FIG. 1. Subsequently, the focus lens 13 is moved in the direction of the optical axis. Then, second focus adjustment is performed such that the phase difference calculated by the phase difference computing unit 33 is within a tolerable range.

At that time, the control unit 32 controls a focus link drive unit of the focus link mechanism 26. When the phase difference calculated by the phase difference computing unit 33 is within the tolerable range, the control unit 32 causes the flip-up mirror 16 to flip up to the position indicated by dashed-dotted line in FIG. 1. Subsequently, the photographing light source 4 is caused via the photographing light source control unit 35 to emit light. Then, an image is captured by the still-image image sensor 17. Further, the image processing unit 31 performs appropriate image processing on the captured image. Then, the processed image is recorded on the memory 36. In addition, a photographed still image is displayed on the monitor 38.

Thus, the fundus camera according to the present embodiment includes the focus target projection unit 8 and the phase difference detection unit 22. Consequently, the fundus camera according to the present embodiment can implement focus adjustment by detecting an error in the focus adjustment performed using the focus target projection unit 8 and the fundus photographing optical system due to an aberration of the subject's eye E.

In a case where the focus target illumination LED 25 is used in the present embodiment as a light source for emitting near-infrared light, a focus target light flux differs in wavelength from a photographing illumination light flux that is visible light emitted from the photographing light source 4. Thus, on the fundus $E_r$ of the subject's eye E, a portion at which the focus target light flux is reflected and scattered differs from a portion at which the photographing illumination light flux is reflected and scattered. Consequently, the control unit 32 does not control the focus link drive unit such that the calculated phase difference is minimized. Instead, the control unit 32 controls the focus link drive unit such that the phase difference is equal to a predetermined value to correct a difference between a portion of the fundus $E_r$ at which the focus target light flux is reflected and scattered and a portion thereof at which the photographing illumination light flux is reflected and scattered.

Further, the control unit 32 is constructed so that, upon completion of driving the focusing lens 13 using the phase difference detection unit 22, the focus target illumination LED 25 is blinked so as to inform the operator of completion of an autofocus operation.

A fundus camera according to another exemplary embodiment of the present invention includes a focus correction switch and a focus lens moving unit. Because the fundus camera includes the focus correction switch, when the focus correction switch is pressed by the operator, the control unit 32 drives the focus lens moving unit based on an output of the phase difference computing unit 33, and controls the focus lens moving unit such that the phase difference is minimized. Incidentally, the focus correction switch can be used also as the photographing switch 37.

Figure 12:
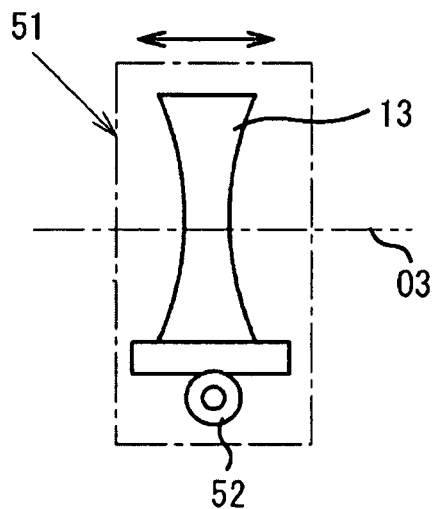
FIG. 12 illustrates a configuration of a focusing lens unit.

FIG. 12 illustrates a focusing lens unit 51. The focusing lens 13 is fixed by a focus lens moving unit 52, which includes a motor, gears, and the like. The focus lens moving unit 52 is constructed to be movable in the direction of the optical axis O3 according to a control signal from the control unit 32, independent of the focus link mechanism 26.

The amount of movement of the focusing lens 13 on the optical axis O3 by the focusing lens moving unit 52 is set to be smaller than that of movement by the focus link mechanism 26. Consequently, the size of the mechanism of the focus lens moving unit 52 can be reduced. Accordingly, the size of the entire fundus camera can be reduced. Furthermore, an operator can achieve focus adjustment with an operational feeling similar to that in the case of operating the conventional fundus camera. In the case of operating the fundus camera according to the present embodiment, a positional relationship between the focus target images Fb and Fc does not change. Thus, the fundus camera according to the present embodiment has an effect of preventing an operator from having an uncomfortable feeling.

When the focus correction switch is pressed, the control unit 32 controls the focus lens moving unit 52 such that the phase difference is minimized. When the phase difference calculated by the phase difference computing unit 33 is within a tolerable value range, the control unit 32 informs an operator of completion of the focus correction with electronic sound or the like. Upon completion of the focus correction, the operator presses the photographing switch 37 and photographs the fundus $E_r$.

Thus, because the fundus camera according to the present embodiment has the focus correction switch, an operator can operate the focus correction switch when focus correction is necessary. Consequently, an operator's unintentional correction can be prevented from being performed. In addition, energy consumption can be suppressed.

The fundus camera according to the present embodiment further includes a warning unit configured to display a warning message on the monitor 38 and/or to make warning sounds, such as buzzer sounds. When the focus correction switch is pressed, the control unit 32 causes the warning unit to issue a warning by making buzzer sounds or blinking the focus target images Fb and Fc, e.g., in a case where the phase difference calculated by the phase difference computing unit 33 is not within a predetermined amount even when the focus lens moving unit 52 is driven. Consequently, the control unit 32 can inform an operator of the difficulty in detecting the phase difference between the focus target images Fb and Fc, and can prompt the operator to photograph the fundus $E_r$ with manual focusing.

According to the present embodiment of the present invention, even when a subject's eye has an intrinsic aberration, the fundus camera can implement higher-precision autofocus by combining detection using a split optical element and phase difference detection, as compared with the conventional fundus camera. Even when correction is made based on phase difference detection, the positional relationship between the focus target images observed by an operator does not change. Thus, the fundus camera according to the present embodiment does not cause an operator to have an uncomfortable feeling. In addition, in a case where it is difficult to detect the phase difference between the focus target images, the warning unit informs an operator of the difficulty in detecting the phase difference therebetween, so that photographing with manual focusing can smoothly be prompted.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-113940 filed Apr. 24, 2008, which is hereby incorporated by reference herein in its entirety.

What is claimed is:

1. A fundus camera comprising:
   a focus target projection unit including a focus target located at a position conjugate with a fundus of a subject's eye, a split optical element configured to split a light flux passing through the focus target to produce a plurality of focus split target light fluxes, and a focus target illumination light source configured to illuminate the focus target;
   a fundus photographing optical system including at least an objective lens, a focusing lens, and a photographic lens;
   sensors configured to be provided at positions which are optically conjugate with an imaging plane of the fundus photographing optical system; and
   a phase difference detection unit configured to detect a phase difference of signals output from the sensors in a case where a plurality of focus target images respectively based on the focus split target light fluxes are located approximately in a line.

2. The fundus camera according to claim 1, further comprising:
   a focus link mechanism configured to interlockingly move the focus target projection unit and the focusing lens in a direction of an optical axis such that the fundus, the focus target, and the imaging plane of the fundus photographing optical system are optically conjugate with one another;
   a focus link drive unit configured to drive the focus link mechanism; and
   a control unit,
   wherein the control unit controls the focus link drive unit based on an output of the phase difference detection unit.

3. The fundus camera according to claim 2, further comprising a focus correction switch,
   wherein the control unit controls the focus link drive unit based on an output of the phase difference detection unit when the focus correction switch is pressed.

4. The fundus camera according to claim 3, further comprising a focusing lens moving unit configured to drive the focusing lens in the direction of the optical axis independent of the focus link mechanism,
   wherein the control unit controls the focusing lens moving unit based on an output of the phase difference detection unit when the focus correction switch is pressed.

5. The fundus camera according to claim 3, further comprising a photographing switch configured to be usable also as the focus correction switch,
   wherein, when the photographing switch is pressed, photographing is performed after the control unit controls the focus link drive unit based on an output of the phase difference detection unit.

6. The fundus camera according to claim 2, wherein the focus target illumination light source includes a light source configured to emit near-infrared light, and
   wherein the control unit controls the focus link drive unit such that the phase difference detected by the phase difference detection unit is equal to a predetermined phase difference.

7. The fundus camera according to claim 2, wherein the control unit causes the focus target illumination light source to blink upon completion of driving the focusing lens by the phase difference detection unit.

8. The fundus camera according to claim 2, wherein the focus link mechanism includes an operation unit operable to manually drive the focus link mechanism.

9. The fundus camera according to claim 4, wherein an amount of movement of the focusing lens by the focus lens moving unit is smaller than that of movement of the focusing lens by the focus link mechanism.

10. The fundus camera according to claim 4, further comprising a warning unit configured to output a warning,
    wherein, when the focus correction switch is pressed, the control unit causes, in a case where the phase difference detected by the phase difference detection unit is not equal to a predetermined amount even when the focusing lens moving unit is controlled, the warning unit to output a warning.

11. The fundus camera according to claim 1, further comprising:
    a driving unit configured to drive the focusing lens based on the phase difference.

12. The fundus camera according to claim 1, further comprising:
    at least two lenses located behind a plane optically conjugate with the imaging plane of the fundus photographing optical system and outside an optical axis of the fundus photographing optical system,
    wherein the image sensors are respectively located behind the at least two lenses.

13. An ophthalmologic apparatus comprising:
    a focus target projection unit configured to project a plurality of focus split target light fluxes based on a focus target onto a subject's eye;
    a sensor unit configured to be provided at positions which are optically conjugate with the focus target projection; and
    a phase difference detection unit configured to detect a phase difference of signals output from the sensor unit in a case where a plurality of focus target images based on the focus split target light fluxes are located approximately in a line.

14. The ophthalmologic apparatus according to claim 13, further comprising a focusing unit located in a photographing optical system; and
    a controlling unit configured to control the focusing unit based on the phase difference after the plurality of focus target images are located approximately in a line.

15. An ophthalmologic apparatus according to claim 13, further comprising:
    a focusing unit located in a photographing optical system;
    a first moving unit configured to move the focus target projection unit to a position where the focus target projection unit is approximately conjugate with the subject's eye;
    a second moving unit configured to move the focusing unit to a position where the focus target projection unit and the photographing unit which is located in the photographing optical system are approximately conjugate with one another; and
    a focus link mechanism configured to mechanically link the first and the second moving units.

16. The ophthalmologic apparatus according to claim 15, further comprising a controlling unit configured to control the focus link mechanism to move the focusing unit to the position where the focus target projection unit and the photographing unit are approximately conjugate with one another after the focus target projection unit is moved to a position where the focus target projection unit is approximately conjugate with the subject's eye.

17. The ophthalmologic apparatus according to claim 13, further comprising:
 a focusing unit located in a photographing optical system;
 an entering unit configured to cause an observation photographing light to enter near an approximate optical axis of an anterior segment of the subject's eye via the illumination optical system; and
 a moving unit configured to move the focusing unit based on displacement in a depth direction between a first focus position of a fundus of the subject's eye by the observation photographing light and a second focus position of the fundus of the subject's eye by the focus index light.

18. The ophthalmologic apparatus according to claim 13, further comprising a plurality of lenses configured to be located outside an optical axis, wherein the plurality of lenses splits light returning from the subject's eye into a plurality of lights outside the optical axis,
 wherein the sensor unit outputs each of the plurality of split lights as the signals.

19. The ophthalmologic apparatus according to claim 18, wherein the sensor unit includes a plurality of one-dimensional sensors each outputting each of the plurality of split lights.

20. The ophthalmologic apparatus according to claim 14, wherein the controlling unit controls the focusing unit such that the phase difference is minimized and controls the focusing unit independently from the focus target projection unit, after the plurality of focus target images are located approximately in a line.

21. An ophthalmologic apparatus comprising:
 a focusing unit located in a photographing optical system;
 a moving unit configured to move the focusing unit along an optical axis of the photographing optical system;
 a focus target projection unit configured to project a plurality of focus split target light fluxes on a subject's eye;
 an acquiring unit configured to acquire a phase difference of at least one of a plurality of focus split target light fluxes in a case where a positional relationship of a plurality of target images respectively based on the plurality of focus split target light fluxes satisfies a predetermined condition; and
 a controlling unit configured to control the moving unit based on the acquired phase difference.

22. The ophthalmologic apparatus according to claim 21, wherein the controlling unit controls the moving unit based on the acquired phase difference in a case where the plurality of target images is aligned.

23. The ophthalmologic apparatus according to claim 21, further comprising: a plurality of lenses configured to be located outside an optical axis, and a phase detection imaging element configured to take an image of the plurality of focus split target light fluxes via the plurality of lenses as a plurality of sensor images
 wherein the acquiring unit acquires the phase difference based on a signal from the phase detection imaging element.

24. The ophthalmologic apparatus according to claim 23, wherein the phase detection imaging element includes a plurality of one-dimensional sensors, and
 wherein the acquiring unit acquires the phase difference based on signals from the plurality of one-dimensional sensors.

25. An The ophthalmologic apparatus according to claim 21,
 wherein the controlling unit controls the moving unit such that the positional relationship satisfies the predetermined condition and controls the moving unit such that the phase difference is decreased, after the positional relationship satisfies the predetermined condition.

26. A method for controlling an ophthalmologic apparatus, the ophthalmologic apparatus including a focusing unit located in a photographing optical system, the method comprising:
 moving the focusing unit along an optical axis of the photographing optical system;
 projecting a plurality of focus split target light fluxes on a subject's eye;
 acquiring a phase difference of at least one of a plurality of focus split target light fluxes in a case where a positional relationship of a plurality of target images respectively based on the plurality of focus split target light fluxes satisfies a predetermined condition; and
 controlling the moving based on the acquired phase difference.

27. A non-transitory computer-readable medium that stores a program of instructions capable of causing a computer to perform the method of claim 26.

28. The ophthalmologic apparatus according to claim 21,
 wherein the acquiring unit acquires a moving amount of the moving unit based on the phase difference after the positional relationship satisfies the predetermined condition, and
 wherein the controlling unit controls the moving unit based on the acquired moving amount.

29. The ophthalmologic apparatus according to claim 21, further comprising:
 a detection unit configured to detect each of the plurality of focus split target light fluxes outside the optical axis of the photographing optical system,
 wherein the acquiring unit acquires the phase difference based on a result of detection by the detection unit.

30. The ophthalmologic apparatus according to claim 29, further comprising:
 a reflection unit disposed in such a way as to be inserted into and removed from an optical path of the photographing optical system,
 wherein the detection unit is disposed in a reflection optical path of the reflection unit, and
 wherein the controlling unit removes the reflection unit from the optical path of the photographing optical system in a case where the controlling unit controls the moving unit based on the phase difference when the reflection unit is in the optical path of the photographing optical system.

31. The ophthalmologic apparatus according to claim 23,
 wherein the plurality of lenses is disposed behind a conjugate surface optically conjugate with an imaging unit, and
 wherein the phase detection imaging element is disposed at a position optically conjugate with the conjugate surface.

32. The ophthalmologic apparatus according to claim 21, further comprising:

a still image acquiring unit configured to photograph the subject's eye and acquire a still image of the subject's eye in a case where the controlling unit controls the moving unit based on the phase difference.

33. The ophthalmologic apparatus according to claim 21, further comprising:
a warning unit configured to issue a warning in a case where the phase difference is not smaller than a predetermined amount.

34. The ophthalmologic apparatus according to claim 21, further comprising:
a target projection moving unit configured to move the focus target projection unit along an optical axis of an illumination optical system,
wherein the controlling unit controls the moving unit independently from the target projection moving unit based on the phase difference.

35. The ophthalmologic apparatus according to claim 21, further comprising:
a target projection moving unit configured to move the focus target projection unit along an optical axis of an illumination optical system; and
a focus ling unit including a mechanism configured to move the moving unit and the target projection moving unit in conjunction with each other.

36. The ophthalmologic apparatus according to claim 35, further comprising:
a focus correction switch configured to output a signal to the focus link unit when the focus correction switch is pressed,
wherein the focus link unit starts the mechanism to move the moving unit and the target projection moving unit.

37. The method according to claim 26, wherein the controlling controls the moving based on the acquired phase difference in a case where the plurality of target images is aligned.

38. The method according to claim 26,
wherein the controlling controls the moving such that the positional relationship satisfies the predetermined condition and controls the moving such that the phase difference is decreased, after the positional relationship satisfies the predetermined condition.

39. The method according to claim 26, further comprising:
detecting each of the plurality of focus split target light fluxes outside the optical axis of the photographing optical system,
wherein the acquiring acquires the phase difference based on a result of detection by the detecting.

40. The method according to claim 26, further comprising:
photographing the subject's eye and acquiring a still image of the subject's eye in a case where the controlling controls the moving based on the phase difference.

41. The method according to claim 26, further comprising:
issuing a warning in a case where the phase difference is not smaller than a predetermined amount.

42. An ophthalmologic photographing apparatus comprising:
a focus target projection unit disposed in an illumination optical system and configured to project a plurality of focus split target light fluxes onto a subject's eye;
a moving unit configured to move a focus unit along an optical axis of a photographing optical system; and
a control unit configured to control, after a positional relationship among a plurality of focus target images corresponding to the plurality of focus split target light fluxes is adjusted, the moving unit so that focus correction suitable for an aberration of the subject's eye is automatically performed.

43. An ophthalmologic photographing method comprising:
adjusting a positional relationship among a plurality of focus target images corresponding to a plurality of focus split target light fluxes projected onto a subject's eye by a focus target projection unit disposed in an illumination optical system; and
controlling, after the positional relationship is adjusted, a moving unit to move a focus unit so that focus correction suitable for an aberration of the subject's eye is automatically performed.

44. A non-transitory computer-readable medium that stores a program of instructions capable of causing a computer to perform the ophthalmologic photographing method of claim 43.

45. The ophthalmologic photographing apparatus according to claim 42, further comprising:
an acquiring unit configured to acquire information indicating a phase in at least one of the plurality of focus target images,
wherein the control unit is configured to control the moving unit based on the information indicating the phase so that the focus correction is performed.

46. The ophthalmologic photographing apparatus according to claim 42, further comprising:
a detection unit disposed behind a conjugate surface optically conjugate with an imaging unit provided in a photographing optical system and configured to detect information indicating a position of the conjugate surface in a direction of an optical axis,
wherein the control unit is configured to control the moving unit based on the detected information so that the focus correction is performed.

47. The ophthalmologic photographing apparatus according to claim 45, further comprising:
a warning unit configured to output a warning in a case where the acquired information does not satisfy a predetermined condition.

48. The ophthalmologic photographing apparatus according to claim 42, wherein the control unit is configured to adjust the positional relationship among the plurality of focus target images so that the plurality of focus target images is located approximately in a line.

49. The ophthalmologic photographing apparatus according to claim 42, further comprising:
a still-image acquiring unit configured to photograph the subject's eye and acquire a still image of the subject's eye after the moving unit is controlled by the control unit.

50. The ophthalmologic photographing method according to claim 43, further comprising:
acquiring information indicating a phase in at least one of the plurality of focus target images,
wherein the control unit is configured to control the moving unit based on the information indicating the phase so that the focus correction is performed.

51. The ophthalmologic photographing method according to claim 50, further comprising:
outputting a warning in a case where the acquired information does not satisfy a predetermined condition.

* * * * *